United States Patent
Sato et al.

(10) Patent No.: US 9,581,604 B2
(45) Date of Patent: Feb. 28, 2017

(54) BIOMARKER FOR ALZHEIMER'S DISEASE OR MILD COGNITIVE IMPAIRMENT

(75) Inventors: Yoshiaki Sato, Tsukuba (JP); Ken Aoshima, Tsukuba (JP); Francois Bernier, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/880,475

(22) PCT Filed: Jun. 23, 2011

(86) PCT No.: PCT/JP2011/064487
§ 371 (c)(1),
(2), (4) Date: Jun. 25, 2013

(87) PCT Pub. No.: WO2012/053255
PCT Pub. Date: Apr. 26, 2012

(65) Prior Publication Data
US 2013/0266589 A1 Oct. 10, 2013

Related U.S. Application Data

(60) Provisional application No. 61/424,885, filed on Dec. 20, 2010.

(30) Foreign Application Priority Data

Oct. 20, 2010 (JP) .................................. 2010-235203
Dec. 20, 2010 (JP) .................................. 2010-282938

(51) Int. Cl.
*G01N 33/92* (2006.01)
*G01N 33/68* (2006.01)

(52) U.S. Cl.
CPC .......... *G01N 33/6896* (2013.01); *G01N 33/92* (2013.01); *Y10T 436/203332* (2015.01)

(58) Field of Classification Search
None
See application file for complete search history.

(56) References Cited

U.S. PATENT DOCUMENTS
2007/0232688 A1 10/2007 Orchansky et al.

FOREIGN PATENT DOCUMENTS
RU 2356058 5/2009
WO WO 03088811 A2 * 10/2003 ......... G01N 33/6887
(Continued)

OTHER PUBLICATIONS

Ahmida et al., Simultaneous determination of plasmatic phytosterols and cholesterol precursors using gas chromatography-mass spectrometry (GC-MS) with selective ion monitoring (SIM). Journal of Chromatography B, 842 (2006) 43-47.*

(Continued)

*Primary Examiner* — Jeffrey Stucker
*Assistant Examiner* — Aurora M Fontainhas
(74) *Attorney, Agent, or Firm* — Fish & Richardson P.C.

(57) ABSTRACT

Desmosterol alone, the combination of desmosterol and amyloid beta, the combination of desmosterol and gelsolin and the combination of desmosterol, amyloid beta and gelsolin can be used as in-blood biomarkers for Alzheimer's disease or mild cognitive impairment. A method for evaluating the effect of a candidate for a therapeutic agent to treat Alzheimer's disease or mild cognitive impairment, a method for aiding the diagnosis of Alzheimer's disease or mild cognitive impairment, and a method for diagnosing Alzheimer's disease or mild cognitive impairment are provided in which the biomarkers are used.

8 Claims, 8 Drawing Sheets

(56) References Cited

FOREIGN PATENT DOCUMENTS

| WO | 2007/097461 | 8/2007 |
| WO | 2007/112573 | 10/2007 |

OTHER PUBLICATIONS

Kolsch et al., Alterations of cholesterol precursor levels in Alzheimer's disease. Biochimica et Biophysica Acta 1801 (2010) 945-950.*

Ussitupa et al., Lathosterol and Other Noncholesterol Sterols During Treatment of Hypercholesterolemia With Lovastatin Alone and With Cholestyramine or Guar Gum. Arteriosclerosis and Thrombosis vol. 12, No. 7 Jul. 1992, 807-813.*

Honda et al., Highly sensitive analysis of sterol profiles in human serum by LC-ESI-MS/MS. Journal of Lipid Research vol. 49, 2008. 2063-2073.*

Suh et al., Therapeutic Agents for Alzheimer's Disease. Curr. Med. Chem.—Central Nervous System Agents, 2005, 5, 259-269.*

Search Report in EP App. Ser. No. 11834097.5, dated Apr. 3, 2014, 7 pages.

Schneider et al., "Biological Marker Candidates of Alzheimer's Disease in Blood, Plasma, and Serum," CNS Neuroscience & Therapeutics, Dec. 1, 2009, 15(4):358-374.

Sato et al., "Identification of a new plasma biomarker of Alzheimer's disease using metabolomics technology," J Lipid Res., Mar. 1, 2012, 53(3):567-576.

Asami et al., "Diagnosis of Alzheimer's disease, Biological Marker Examination, Blood Aβ", Japan Journal of Clinical Medicine, vol. 66 special extra issue I, Jan. 28, 2008, p. 232-p. 236 (with English translation).

Benvenuti et al., "Neuronal differentiation of human mesenchymal stem cells: Changes in the expression of the Alzheimer's disease-related gene seladin-1", Exp Cell Res, (2006) 312(13):2592-2604.

Bouwman et al., "CSF biomarker levels in early and late onset Alzheimer's disease", Neurobiol. of Aging., 2009; 30(12):1895-1901.

Guentert et al., "Plasma Gelsolin is Decreased and Correlates with Rate of Decline in Alzheimer's Disease", J. Alzheimer's. Dis., (2010) 21(2):585-596.

Ibach et al., "Cerebrospinal fluid tau and beta-amyloid in Alzheimer patients, disease controls and an age-matched random sample", Neurobiol. of Aging., 2006;. 27( 9):1202-1211.

International Preliminary Report on Patentability for PCT/JP2011/064487 dated May 16, 2013.

International Search Report for PCT/JP2011/064487 dated Aug. 9, 2011.

Kölsch et al., "Alterations of cholesterol precursor levels in Alzheimer's disease", Biochim. Biophys. Acta, (2010) 1801(8): 945-950.

Kuriyama et al., "Serum Lipids, Lipoproteins and Apoliporoteins in Patients with Senile Dementia", Japanese Journal of Geriatrics, (1992) 29(7-8):559-564 (with English translation).

Levi et al., "Regulation of hippocampal cholesterol metabolism by apoE and environmental stimulation", Neurochem., (2005) 95(4):987-997.

Sato et al., "Discovery of Novel Biomarker for Alzheimer's disease Using Metabolomics", Abstracts of the 23rd Symposium on Bio-medical-Analytical Sciences, Jul. 21, 2010, 23:196-197 (with English translation).

Mikio Shoji, "Clinical approach and pathological cascabe of dementia," Clinical Neurology, 2008, 48:467-475 (English Abstract).

Response to Office Action in CA App. Ser. No. 2814385, dated Dec. 22, 2015, 11 pages.

Office Action in CA App. Ser. No. 2814385, dated Jul. 7, 2015, 4 pages.

Response to Office Action in EP App. Ser. No. 11834097.5, dated Jun. 12, 2015, 30 pages.

Response to Office Action in RU App. Ser. No. 2013122853, dated Apr. 20, 2015, 5 pages (with English summary).

Lutjohann et al., "24S-hydroxycholesterol: a marker of brain cholesterol metabolism," Pharamacopsychiatry, 2003, 36(Suppl 2):S102-S106.

Notice of Allowance in RU App. Ser. No. 2013122853, dated Jun. 1, 2015, 12 pages (with English translation).

Response to Examiner's Report in AU App. Ser. No. 2011319319, dated Jul. 15, 2015, 3 pages.

Notice of Allowance in AU App. Ser. No. 2011319319, dated Jul. 21, 2015, 3 pages.

Kolsch et al., "Alterations of Brain Cholesterol Metabolism: Relevance of Desmosterol in Alzheimer's Disease and Vascular Dementia," Alzheimer's and Dementia, 2(3Supplement):S278, P2-153, Jul. 2006.

Office Action in Canadian Application No. 2814385, dated Mar. 7, 2016, 2 pages.

Response to Office Action in CA App. Ser. No. 2814385, dated Sep. 7, 2016, 19 pages.

Office Action in Canadian Application No. 2814385, dated Nov. 21, 2016, 3 pages.

* cited by examiner

BIOMARKER FOR ALZHEIMER'S DISEASE OR MILD COGNITIVE IMPAIRMENT

TECHNICAL FIELD

The present invention relates to a biomarker for Alzheimer's disease or mild cognitive impairment. More specifically, the present invention relates to a method for evaluating the effect of a candidate for a therapeutic agent for Alzheimer's disease or mild cognitive impairment, a method for aiding the diagnosis of Alzheimer's disease or mild cognitive impairment, and a method for diagnosing Alzheimer's disease or mild cognitive impairment.

BACKGROUND ART

A biomarker is very useful for diagnosing and monitoring the progress of a disease, and is important for screening patients, monitoring side effects, aiding for the selection of an appropriate treatment and discovering a new drug. In Alzheimer's disease, Aβ (amyloid beta) 1-42 and phosphorylated tau protein in the cerebrospinal fluid are currently considered to be the most useful biomarkers (Non Patent Literatures 1 and 2).

CITATION LIST

Non Patent Literature

Non Patent Literature 1: Ibach et al., "Cerebrospinal fluid tau and beta-amyloid in Alzheimer patients, disease controls and an age-matched random sample," Neurobiol. Aging., 2006; vol. 27 (no. 9): p. 1202-1211.

Non Patent Literature 2: Bouwman et al., "CSF biomarker levels in early and late onset Alzheimer's disease," Neurobiol. Aging., 2009; vol. 30 (no. 12): p. 1895-1901.

Non Patent Literature 3: Koelsch et al. "Alterations of cholesterol precursor levels in Alzheimer's disease," Biochim. Biophys. Acta., 2010; vol. 1801 (no. 8): p. 945-950.

Non Patent Literature 4: Guentert et al., "Plasma Gelsolin is Decreased and Correlates with Rate of Decline in Alzheimer's Disease," J. Alzheimer's. Dis., 2010; vol. 21 (no. 2): p. 585-596.

SUMMARY OF INVENTION

Technical Problem

However, for the above biomarkers, use of the cerebrospinal fluid is required, and, in particular, collecting the cerebrospinal fluid every time the time-dependent change of Alzheimer pathology is monitored imposes an enormous burden on the patient, and thus a low invasive biomarker using blood or the like, has been demanded.

Solution to Problem

Desmosterol is a precursor of cholesterol. In Alzheimer's disease, it is thought that the disorder of cholesterol metabolism has occurred, and documented that the desmosterol level in the cerebrospinal fluid of patients with Alzheimer's disease is lower than that of healthy elderly people, while the desmosterol level in the plasma remains unchanged (Non Patent Literature 3). The present inventors found that, inconsistent with this finding, the desmosterol level in plasma of patients with Alzheimer's disease is lower than that of healthy elderly people, and the desmosterol in plasma can be used as a biomarker for Alzheimer's disease. Further, the present inventors found that desmosterol alone enables diagnosis of the mild cognitive impairment, manifesting the mild cognitive dysfunction which is a pre-existing disease of Alzheimer's disease.

Furthermore, the present inventors found that the combination of desmosterol and amyloid beta in blood when used as a biomarker enables more accurate diagnosis of Alzheimer's disease or mild cognitive impairment than when desmosterol alone in blood is used as a biomarker.

Furthermore, the present inventors found that the combination of desmosterol and gelsolin in blood, or the combination of desmosterol, amyloid beta and gelsolin in blood, when used as a biomarker, enables more accurate diagnosis of Alzheimer's disease or mild cognitive impairment than when desmosterol alone in blood is used as a biomarker. It is known that the plasma gelsolin level is low in patients with Alzheimer's disease (Non Patent Literature 4).

Specifically, the present invention provides the following [1] to [28].

[1] A method for evaluating an effect of a candidate for a therapeutic agent to treat Alzheimer's disease or mild cognitive impairment, the method comprising:
a step of measuring a desmosterol level in blood of a non-human animal;
a step of administering a candidate to the non-human animal;
a step of measuring a desmosterol level in blood of the non-human animal after the candidate is administered; and
a step of providing an indicator of being potential for the candidate to be effective in treating Alzheimer's disease or mild cognitive impairment when the desmosterol level in blood of the non-human animal after the candidate is administered is higher than the level before the candidate is administered.

[2] A method for evaluating an effect of a candidate for a therapeutic agent to treat Alzheimer's disease or mild cognitive impairment, the method comprising:
a step of measuring a desmosterol level in blood of a first non-human animal;
a step of administering a candidate to a second non-human animal;
a step of measuring a desmosterol level in blood of the second non-human animal after the candidate is administered; and
a step of providing an indicator of being potential for the candidate to be effective in treating Alzheimer's disease or mild cognitive impairment when the desmosterol level in blood of the second non-human animal after the candidate is administered is higher than the desmosterol level in blood of the first non-human animal to which the candidate is not administered.

[3] A method for evaluating an effect of a candidate for a therapeutic agent to treat Alzheimer's disease or mild cognitive impairment, the method comprising:
a step of measuring a desmosterol level in a blood sample of a subject before a candidate is administered;
a step of measuring a desmosterol level in the blood sample of the subject after the candidate is administered; and
a step of providing an indicator of being potential for the candidate to be effective in treating Alzheimer's disease or mild cognitive impairment when the desmosterol level in blood of the subject after the candidate is administered is higher than the desmosterol level in blood before the candidate is administered.

[4] A method for aiding diagnosis of Alzheimer's disease or mild cognitive impairment, the method comprising:

a step of measuring a desmosterol level in a blood sample of a subject; and a step of providing an indicator for potentially having Alzheimer's disease or mild cognitive impairment when the desmosterol level in blood of the subject is lower than a reference value.

[5] A method for diagnosing Alzheimer's disease or mild cognitive impairment, the method comprising:
a step of measuring a desmosterol level in blood of a subject; and
a step of identifying Alzheimer's disease or mild cognitive impairment when the desmosterol level in blood of the subject is lower than a reference value.

[6] A method for selecting a patient which is likely to benefit from a therapeutic effect of a candidate for a therapeutic agent to treat Alzheimer's disease or mild cognitive impairment, the method comprising:
a step of measuring a desmosterol level in a blood sample of a subject; and
a step of providing an indicator of a patient to be administered with a candidate for a therapeutic agent to treat Alzheimer's disease or mild cognitive impairment when the desmosterol level in blood of the subject is lower than a reference value.

[7] A method for predicting a therapeutic effect of a candidate for a therapeutic agent to treat Alzheimer's disease or mild cognitive impairment, the method comprising:
a step of measuring a desmosterol level in a blood sample of a subject; and
a step of providing an indicator of being potential for the candidate to be effective in treating Alzheimer's disease or mild cognitive impairment when the desmosterol level in blood of the subject is lower than a reference value.

[8] A method for evaluating an effect of a candidate for a therapeutic agent to treat Alzheimer's disease or mild cognitive impairment, the method comprising:
a step of measuring a desmosterol level and an amyloid beta level in blood of a non-human animal;
a step of administering a candidate to the non-human animal;
a step of measuring a desmosterol level and an amyloid beta level in blood of the non-human animal after the candidate is administered; and
a step of providing an indicator of being potential for the candidate to be effective in treating Alzheimer's disease or mild cognitive impairment when the desmosterol level in blood of the non-human animal after the candidate is administered is higher than the level before the candidate is administered, and Aβx-42 or Aβx-42/Aβx-40 in blood of the non-human animal after the candidate is administered is higher than that before the candidate is administered.

[9] A method for evaluating an effect of a candidate for a therapeutic agent to treat Alzheimer's disease or mild cognitive impairment, the method comprising:
a step of measuring a desmosterol level and an amyloid beta level in blood of a first non-human animal;
a step of administering a candidate to a second non-human animal;
a step of measuring a desmosterol level and an amyloid beta level in blood of the second non-human animal after the candidate is administered; and
a step of providing an indicator of being potential for the candidate to be effective in treating Alzheimer's disease or mild cognitive impairment when the desmosterol level in blood of the second non-human animal after the candidate is administered is higher than the desmosterol level in blood of the first non-human animal to which the candidate is not administered, and Aβx-42 or Aβx-42/Aβx-40 in blood of the second non-human animal after the candidate is administered is higher than Aβx-42 or Aβx-42/Aβx-40 in blood of the first non-human animal to which the candidate is not administered.

[10] A method for evaluating an effect of a candidate for a therapeutic agent to treat Alzheimer's disease or mild cognitive impairment, the method comprising:
a step of measuring a desmosterol level and an amyloid beta level in a blood sample of a subject before a candidate is administered;
a step of measuring a desmosterol level and an amyloid beta level in the blood sample of the subject after the candidate is administered; and
a step of providing an indicator of being potential for the candidate to be effective in treating Alzheimer's disease or mild cognitive impairment when the desmosterol level in blood of the subject after the candidate is administered is higher than the desmosterol level in blood before the candidate is administered, and Aβx-42 or Aβx-42/Aβx-40 in blood of the subject after the candidate is administered is higher than that before the candidate is administered.

[11] A method for aiding diagnosis of Alzheimer's disease or mild cognitive impairment, the method comprising:
a step of measuring a desmosterol level and an amyloid beta level in a blood sample of a subject and
a step of providing an indicator for potentially having Alzheimer's disease or mild cognitive impairment when the desmosterol level in blood of the subject is lower than a reference value, and Aβx-42 or Aβx-42/Aβx-40 in blood of the subject is lower than a reference value.

[12] A method for diagnosing Alzheimer's disease or mild cognitive impairment, the method comprising:
a step of measuring a desmosterol level and an amyloid beta level in blood of a subject; and
a step of identifying Alzheimer's disease or mild cognitive impairment when the desmosterol level in blood of the subject is lower than a reference value, and Aβx-42 or Aβx-42/Aβx-40 in blood of the subject is lower than a reference value.

[13] A method for selecting a patient which is likely to benefit from a therapeutic effect of a candidate for a therapeutic agent to treat Alzheimer's disease or mild cognitive impairment, the method comprising:
a step of measuring a desmosterol level and an amyloid beta level in a blood sample of a subject; and
a step of providing an indicator of a patient to be administered with a candidate for a therapeutic agent to treat Alzheimer's disease or mild cognitive impairment when the desmosterol level in blood of the subject is lower than a reference value, and Aβx-42 or Aβx-42/Aβx-40 in blood of the subject is lower than a reference value.

[14] A method for predicting a therapeutic effect of a candidate for a therapeutic agent to treat Alzheimer's disease or mild cognitive impairment, the method comprising:
a step of measuring a desmosterol level and an amyloid beta level in a blood sample of a subject; and
a step of providing an indicator of being potential for the candidate to be effective in treating Alzheimer's disease or mild cognitive impairment when the desmosterol level in blood of the subject is lower than a reference value, and Aβx-42 or Aβx-42/Aβx-40 in blood of the subject is lower than a reference value.

[15] A method for evaluating an effect of a candidate for a therapeutic agent to treat Alzheimer's disease or mild cognitive impairment, the method comprising:

a step of measuring a desmosterol level, an amyloid beta level and a gelsolin level in blood of a non-human animal;

a step of administering a candidate to the non-human animal;

a step of measuring a desmosterol level, an amyloid beta level and a gelsolin level in blood of the non-human animal after the candidate is administered; and a step of providing an indicator of being potential for the candidate to be effective in treating Alzheimer's disease or mild cognitive impairment when the desmosterol level in blood of the non-human animal after the candidate is administered is higher than the desmosterol level in blood before the candidate is administered, Aβx-42 or Aβx-42/Aβx-40 in blood of the non-human animal after the candidate is administered is higher than that before the candidate is administered, and the gelsolin level in blood of the non-human animal after the candidate is administered is higher than the gelsolin level in blood before the candidate is administered.

[16] A method for evaluating an effect of a candidate for a therapeutic agent to treat Alzheimer's disease or mild cognitive impairment, the method comprising:

a step of measuring a desmosterol level, an amyloid beta level and a gelsolin level in blood of a first non-human animal;

a step of administering a candidate to a second non-human animal;

a step of measuring a desmosterol level, an amyloid beta level and a gelsolin level in blood of the second non-human animal after the candidate is administered; and a step of providing an indicator of being potential for the candidate to be effective in treating Alzheimer's disease or mild cognitive impairment when the desmosterol level in blood of the second non-human animal after the candidate is administered is higher than the desmosterol level in blood of the first non-human animal to which the candidate is not administered, Aβx-42 or Aβx-42/Aβx-40 in blood of the second non-human animal after the candidate is administered is higher than Aβx-42 or Aβx-42/Aβx-40 in blood of the first non-human animal to which the candidate is not administered, and the gelsolin level in blood of the second non-human animal after the candidate is administered is higher than the gelsolin level in blood of the first non-human animal to which the candidate is not administered.

[17] A method for evaluating an effect of a candidate for a therapeutic agent to treat Alzheimer's disease or mild cognitive impairment, the method comprising:

a step of measuring a desmosterol level, an amyloid beta level and a gelsolin level in a blood sample of a subject before a candidate is administered, a step of measuring a desmosterol level, an amyloid beta level and a gelsolin level in the blood sample of the subject after the candidate is administered, a step of providing an indicator of being potential for the candidate to be effective in treating Alzheimer's disease or mild cognitive impairment when the desmosterol level in blood of the subject after the candidate is administered is higher than the desmosterol level before the candidate is administered, Aβx-42 or Aβx-42/Aβx-40 in blood of the subject after the candidate is administered is higher than that before the candidate is administered, and the gelsolin level in blood of the subject after the candidate is administered is higher than the gelsolin level in blood before the candidate is administered.

[18] A method for aiding diagnosis of Alzheimer's disease or mild cognitive impairment; the method comprising:

a step of measuring a desmosterol level, an amyloid beta level and a gelsolin level in a blood sample of a subject; and a step of providing an indicator for potentially having Alzheimer's disease or mild cognitive impairment when the desmosterol level in blood of the subject is lower than a reference value, Aβx-42 or Aβx-42/Aβx-40 in blood of the subject is lower than a reference value, and the gelsolin level in blood of the subject is lower than a reference value.

[19] A method for diagnosing Alzheimer's disease or mild cognitive impairment, the method comprising:

a step of measuring a desmosterol level, an amyloid beta level and a gelsolin level in blood of a subject; and a step of identifying Alzheimer's disease or mild cognitive impairment when the desmosterol level in blood of the subject is lower than a reference value, Aβx-42 or Aβx-42/Aβx-40 in blood of the subject is lower than a reference value, and the gelsolin level in blood of the subject is lower than a reference value.

[20] A method for selecting a patient which is likely to benefit from a therapeutic effect of a candidate for a therapeutic agent to treat Alzheimer's disease or mild cognitive impairment, the method comprising:

a step of measuring a desmosterol level, an amyloid beta level and a gelsolin level in a blood sample of a subject; and a step of providing an indicator of a patient to be administered with a candidate for a therapeutic agent to treat Alzheimer's disease or mild cognitive impairment when the desmosterol level in blood of the subject is lower than a reference value, Aβx-42 or Aβx-42/Aβx-40 in blood of the subject is lower than a reference value, and the gelsolin level in blood of the subject is lower than a reference value.

[21] A method for predicting a therapeutic effect of a candidate for a therapeutic agent to treat Alzheimer's disease or mild cognitive impairment, the method comprising:

a step of measuring a desmosterol level, an amyloid beta level and a gelsolin level in a blood sample of a subject, and a step of providing an indicator of being potential for the candidate to be effective in treating Alzheimer's disease or mild cognitive impairment when the desmosterol level in blood of the subject is lower than a reference value, Aβx-42 or Aβx-42/Aβx-40 in blood of the subject is lower than a reference value, and the gelsolin level in blood of the subject is lower than a reference value.

[22] A method for evaluating an effect of a candidate for a therapeutic agent to treat Alzheimer's disease or mild cognitive impairment, the method comprising:

a step of measuring a desmosterol level and a gelsolin level in blood of a non-human animal;

a step of administering a candidate to the non-human animal;

a step of measuring a desmosterol level and a gelsolin level in blood of the non-human animal after the candidate is administered; and a step of providing an indicator of being potential for the candidate to be effective in treating Alzheimer's disease or mild cognitive impairment when the desmosterol level in blood of the non-human animal after the candidate is administered is higher than the desmosterol level in blood before the candidate is administered, and the gelsolin level in blood of the non-human animal after the candidate is administered is higher than the gelsolin level in blood before the candidate is administered.

[23] A method for evaluating an effect of a candidate for a therapeutic agent to treat Alzheimer's disease or mild cognitive impairment, the method comprising:

a step of measuring a desmosterol level and a gelsolin level in blood of a first non-human animal;

a step of administering a candidate to a second non-human animal;

a step of measuring a desmosterol level and a gelsolin level in blood of the second non-human animal after the candidate is administered; and a step of providing an indicator of being potential for the candidate to be effective in treating Alzheimer's disease or mild cognitive impairment when the desmosterol level in blood of the second non-human animal after the candidate is administered is higher than the desmosterol level in blood of the first non-human animal to which the candidate is not administered, and the gelsolin level in blood of the second non-human animal after the candidate is administered is higher than the gelsolin level in blood of the first non-human animal to which the candidate is not administered.

[24] A method for evaluating an effect of a candidate for a therapeutic agent to treat Alzheimer's disease or mild cognitive impairment, the method comprising:

a step of measuring a desmosterol level and a gelsolin level in a blood sample of a subject before a candidate is administered;

a step of measuring a desmosterol level and a gelsolin level in the blood sample of the subject after the candidate is administered; and a step of providing an indicator of being potential for the candidate to be effective in treating Alzheimer's disease or mild cognitive impairment when the desmosterol level in blood of the subject after the candidate is administered is higher than the desmosterol level in blood before the candidate is administered, and the gelsolin level in blood of the subject after the candidate is administered is higher than the gelsolin level in blood before the candidate is administered.

[25] A method for aiding diagnosis of Alzheimer's disease or mild cognitive impairment, the method comprising:

a step of measuring a desmosterol level and a gelsolin level in a blood sample of a subject; and a step of providing an indicator for potentially having Alzheimer's disease or mild cognitive impairment when the desmosterol level in blood of the subject is lower than a reference value, and the gelsolin level in blood of the subject is lower than a reference value.

[26] A method for diagnosing Alzheimer's disease or mild cognitive impairment, the method comprising:

a step of measuring a desmosterol level and a gelsolin level in blood of a subject; and a step of identifying Alzheimer's disease or mild cognitive impairment when the desmosterol level in blood of the subject is lower than a reference value, and the gelsolin level in blood of the subject is lower than a reference value.

[27] A method for selecting a patient which is likely to benefit from a therapeutic effect of a candidate for a therapeutic agent to treat Alzheimer's disease or mild cognitive impairment, the method comprising:

a step of measuring a desmosterol level and a gelsolin level in a blood sample of a subject; and a step of providing an indicator of a patient to be administered with a candidate for a therapeutic agent to treat Alzheimer's disease or mild cognitive impairment when the desmosterol level in blood of the subject is lower than a reference value, and the gelsolin level in blood of the subject is lower than a reference value.

[28] A method for predicting a therapeutic effect of a candidate for a therapeutic agent to treat Alzheimer's disease or mild cognitive impairment, the method comprising:

a step of measuring a desmosterol level and a gelsolin level in a blood sample of a subject; and a step of providing an indicator of being potential for the candidate to be effective in treating Alzheimer's disease or mild cognitive impairment when the desmosterol level in blood of the subject is lower than a reference value, and the gelsolin level in blood of the subject is lower than a reference value.

Advantageous Effects of Invention

Using a desmosterol level in blood, or the like, as an indicator, it is possible to diagnose accurately the progress of Alzheimer's disease or mild cognitive impairment, it is also possible to evaluate accurately an effect of a candidate for a therapeutic agent to treat Alzheimer's disease or mild cognitive impairment, it is further possible to select a patient which is likely to benefit from the therapeutic effect of a candidate for a therapeutic agent to treat Alzheimer's disease or mild cognitive impairment, and it is furthermore possible to predict the therapeutic effect of a candidate for a therapeutic agent to treat Alzheimer's disease or mild cognitive impairment. The desmosterol and the like, of the present invention are the biomarkers in blood, and it is thus possible to diagnose accurately Alzheimer's disease or mild cognitive impairment without collecting the cerebrospinal fluid.

DESCRIPTION OF EMBODIMENTS

Figure 1:
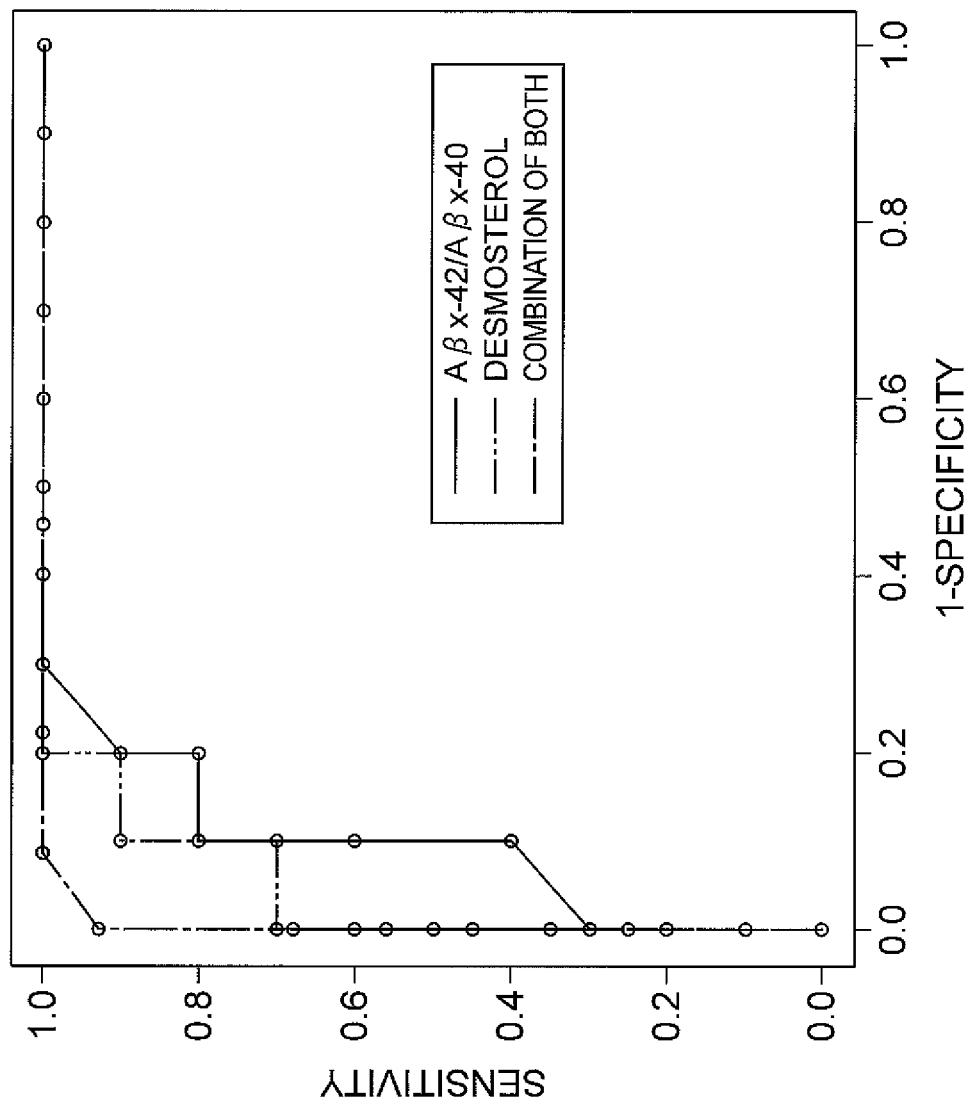
FIG. 1 is a chart showing the Receiver Operating Characteristic Curves of desmosterol, Aβx-42/Aβx-40 and the combination thereof in healthy elderly people and patients with Alzheimer's disease.

The method for evaluating an effect of a candidate for a therapeutic agent to treat Alzheimer's disease or mild cognitive impairment of the present invention targets a non-human animal or a human. It is preferable that the non-human animal be a mammal. It is preferable that the non-human animal be a model animal with Alzheimer's disease or mild cognitive impairment. Examples of the model animal with Alzheimer's disease or mild cognitive impairment include an animal with an increased production of amyloid beta by the modification of amyloid precursor protein (APP) or presenilin 2. More specifically, an example includes Tg2576, a genetically modified mouse overexpressing APP. It is preferable that the human be a patient with Alzheimer's disease or mild cognitive impairment.

The effect of a candidate can be evaluated when a desmosterol level in blood of a non-human animal or a human of the same individual is measured before and after the candidate is administered and the levels are compared.

The desmosterol level in blood used herein can be measured by the liquid chromatography/mass spectrometry (LC/MS). More specifically, it can be measured under the conditions described in Examples. The desmosterol level in blood may be a concentration of desmosterol, or desmosterol/cholesterol, which is the ratio of desmosterol to cholesterol, with a concentration of desmosterol being preferable. Also, the desmosterol level in blood can be measured by the Enzyme-Linked ImmunoSorbent Assay (ELISA) or gas chromatography/mass spectrometry (GC-MS). The desmosterol level in blood is preferably a level in plasma.

The candidate drug efficacy can be evaluated based on an indicator of being potential for the candidate to be effective in treating Alzheimer's disease or mild cognitive impairment when the desmosterol level in blood after the candidate is administered is higher than the desmosterol level in blood before the candidate is administered.

Further, using non-human animals of different individuals, the effect of a candidate can be evaluated by measuring desmosterol levels in blood of one or a plurality of individuals in one group without administering the candidate (control group), measuring desmosterol levels in blood of one or a plurality of individuals of the other group after the candidate is administered (candidate-administered group), and comparing the levels of those groups. In this instance, the candidate drug efficacy can be evaluated based on an indicator of being potential for the candidate to be effective in treating Alzheimer's disease or mild cognitive impairment when the desmosterol level in blood is higher in the candidate-administered group than the desmosterol level in blood in the control group.

The method for aiding diagnosis of Alzheimer's disease or mild cognitive impairment of the present invention provides an indicator for diagnosis by measuring a desmosterol level in a blood sample of a subject which is suspected to have Alzheimer's disease or mild cognitive impairment and comparing a reference value therewith. More specifically, the method of the present invention provides an indicator for potentially having Alzheimer's disease or mild cognitive impairment when the desmosterol level in blood of the subject is lower than a reference value. A reference value of desmosterol level in blood can be determined by referring to the values of a patient definitely diagnosed with Alzheimer's disease or mild cognitive impairment and of a healthy person.

The method for diagnosing Alzheimer's disease or mild cognitive impairment of the present invention makes identification by measuring a desmosterol level of a subject which is suspected to have Alzheimer's disease or mild cognitive impairment and comparing a reference value therewith. More specifically, when the desmosterol level in blood of the subject is lower than a reference value, the subject is identified as having Alzheimer's disease or mild cognitive impairment. The reference value of desmosterol level in blood is as described above.

The method for selecting a patient which is likely to benefit from the therapeutic effect of a candidate for a therapeutic agent to treat Alzheimer's disease or mild cognitive impairment of the present invention makes identification by measuring a desmosterol level in blood of a subject which is diagnosed with Alzheimer's disease or mild cognitive impairment and comparing a reference value therewith. More specifically, the selection can be made based on an indicator of a patient to be administered with the candidate for the therapeutic agent to treat Alzheimer's disease or mild cognitive impairment when the desmosterol level in blood of the subject is lower than a reference value. The reference value of desmosterol level in blood is as described above.

The method for predicting the therapeutic effect of a candidate for a therapeutic agent to treat Alzheimer's disease or mild cognitive impairment of the present invention makes identification by measuring a desmosterol level in blood of a subject which is diagnosed with Alzheimer's disease or mild cognitive impairment and comparing a reference value therewith. More specifically, the prediction can be made based on an indicator of being potential for the candidate to be effective in treating Alzheimer's disease or mild cognitive impairment when the desmosterol level in blood of the subject is lower than a reference value. The reference value of desmosterol level in blood is as described above.

The candidate for the therapeutic agent to treat Alzheimer's disease or mild cognitive impairment of the present invention is not particularly limited, and is preferably a modulator of the cholesterol metabolism pathway or a modulator based on Aβ hypothesis, more preferably a (β-secretase inhibitor, a γ-secretase inhibitor, a γ-secretase modulator, anti-Aβ antibody, anti-Aβ oligomer antibody and the like.

In the above methods, a desmosterol level alone in blood may be used as a biomarker, or may be used in combination with other biomarkers. More accurate evaluation or the like, can be carried out when a desmosterol level in blood is combined with other biomarkers. In particular, the combination with an amyloid beta level in blood, the combination with gelsolin level in blood, or the combination with an amyloid beta level and a gelsolin level in blood enables a significantly accurate evaluation or the like, to be carried out, hence preferable. Hereinbelow, embodiments using the combination with these biomarkers are described in detail.

The method, which uses a desmosterol level and amyloid beta level in blood as the biomarkers, is described.

The method for evaluating an effect of a candidate for a therapeutic agent to treat Alzheimer's disease or mild cognitive impairment of the present invention targets a non-human animal or a human. Specifics are as described above.

The effect of a candidate can be evaluated when a desmosterol level and an amyloid beta level in blood of a non-human animal or a human of the same individual are measured before and after the candidate is administered and the levels are compared.

The method for measuring a desmosterol level in blood is as described above.

The amyloid beta level in blood can be measured, for example, by known methods such as ELISA or LC/MS. It is desirable that the amyloid beta be measured in both Aβx-40 and Aβx-42. Aβx-40 means Aβ1-40 and a peptide having the N-terminus thereof is partially deleted, and Aβx-42 means Aβ1-42 and a peptide having the N-terminus thereof is partially deleted. The amyloid beta level in blood may be a concentration of Aβx-42 in blood, or may be Aβx-42/Aβx-40, which is the ratio of Aβx-42 to Aβx-40, with Aβx-42/Aβx-40 being preferable. The amyloid beta level in blood is preferably a level in plasma.

The candidate drug efficacy can be evaluated based on an indicator of being potential for the candidate to be effective in treating Alzheimer's disease or mild cognitive impairment when the desmosterol level in blood after the candidate is administered is higher than the desmosterol level in blood before the candidate is administered, and Aβx-42 or Aβx-42/Aβx-40 in blood after the candidate is administered is higher than that before the candidate is administered. The Aβx-42/Aβx-40 in blood means a ratio of the Aβx-42 level in blood to the Aβx-40 level in blood.

Also, using non-human animals of different individuals, the effect of a candidate can be evaluated by measuring desmosterol levels and amyloid beta levels in blood of one or a plurality of individuals in one group without administering the candidate (control group), measuring desmosterol levels and amyloid beta levels in blood of one or a plurality of individuals of the other group after the candidate is administered (candidate-administered group), and comparing the levels of those groups. In this instance, the candidate drug efficacy can be evaluated based on an indicator of being potential for the candidate to be effective in treating Alzheimer's disease or mild cognitive impairment when the desmosterol level in blood of the candidate-administered group is higher than the level of the control group, and Aβx-42 or Aβx-42/Aβx-40 in blood of the candidate-administered group is higher than that of the control group.

The method for aiding diagnosis of Alzheimer's disease or mild cognitive impairment of the present invention provides an indicator for diagnosis by measuring a desmosterol level and an amyloid beta level in a blood sample of a subject which is suspected to have Alzheimer's disease or mild cognitive impairment and comparing reference values therewith. More specifically, the method of the present invention provides an indicator for potentially having Alzheimer's disease or mild cognitive impairment when the desmosterol level in blood of the subject is lower than a reference value, and Aβx-42 or Aβx-42/Aβx-40 in blood of the subject is lower than a reference value. The reference value of desmosterol level in blood and the reference value of Aβx-42 or Aβx-42/Aβx-40 in blood can be determined by referring to the value of a patient definitely diagnosed with Alzheimer's disease or mild cognitive impairment.

The method for diagnosing Alzheimer's disease or mild cognitive impairment of the present invention makes identification by measuring a desmosterol level and an amyloid beta level in blood of a subject which is suspected to have Alzheimer's disease or mild cognitive impairment and comparing reference values therewith. More specifically, when the desmosterol level in blood of the subject is lower than a reference value, and Aβx-42 or Aβx-42/Aβx-40 in blood of the subject is lower than a reference value, the subject is identified as having Alzheimer's disease or mild cognitive impairment. The reference value of desmosterol level in blood and the reference value of Aβx-42 or Aβx-42/Aβx-40 in blood are as described above.

The method for selecting a patient which is likely to benefit from the therapeutic effect of a candidate for a therapeutic agent to treat Alzheimer's disease or mild cognitive impairment of the present invention makes identification by measuring a desmosterol level and an amyloid beta level in blood of a subject which is diagnosed with Alzheimer's disease or mild cognitive impairment and comparing reference values therewith. More specifically, the selection can be made based on an indicator of a patient to be administered with the candidate for a therapeutic agent to treat Alzheimer's disease or mild cognitive impairment when the desmosterol level in blood of the subject is lower than a reference value, and Aβx-42 or Aβx-42/Aβx-40 in blood of the subject is lower than a reference value. The reference value of desmosterol level in blood and the reference value of Aβx-42 or Aβx-42/Aβx-40 in blood are as described above.

The method for predicting the therapeutic effect of a candidate for a therapeutic agent to treat Alzheimer's disease or mild cognitive impairment of the present invention makes identification by measuring a desmosterol level and an amyloid beta level in blood of a subject which is diagnosed with Alzheimer's disease or mild cognitive impairment and comparing reference values therewith. More specifically, the prediction can be made based on an indicator of being potential for the candidate to be effective in treating Alzheimer's disease or mild cognitive impairment when the desmosterol level in blood of the subject is lower than a reference value, and the Aβx-42 or Aβx-42/Aβx-40 in blood of the subject is lower than a reference value. The reference value of desmosterol level in blood and the reference value of Aβx-42 or Aβx-42/Aβx-40 in blood are as described above.

The candidate for a therapeutic agent to treat Alzheimer's disease or mild cognitive impairment of the present invention is not particularly limited, and is preferably as described above.

The method, which uses a desmosterol level, an amyloid beta level and a gelsolin level in blood as the biomarkers, is described.

The method for evaluating an effect of a candidate for a therapeutic agent to treat Alzheimer's disease or mild cognitive impairment of the present invention targets a non-human animal or a human. Specifics are as described above.

The effect of a candidate can be evaluated when a desmosterol level, an amyloid beta level and a gelsolin level in blood of a non-human animal or a human of the same individual are measured before and after the candidate is administered and the levels are compared.

The method for measuring a desmosterol level and an amyloid beta level in blood is as described above.

The gelsolin level in blood can be measured, for example, by known methods such as ELISA. The gelsolin level in blood is preferably a level in plasma, The candidate drug efficacy can be evaluated based on an indicator of being potential for the candidate to be effective in treating Alzheimer's disease or mild cognitive impairment when the desmosterol level in blood after the candidate is administered is higher than the desmosterol level in blood before the candidate is administered, Aβx-42 or Aβx-42/Aβx-40 in blood after the candidate is administered is higher than that before the candidate is administered, and the gelsolin level in blood after the candidate is administered is higher than the gelsolin level in blood before the candidate is administered.

Also, using non-human animals of different individuals, the effect of a candidate can be evaluated by measuring desmosterol levels, amyloid beta levels and gelsolin levels in blood of one or a plurality of individuals in one group without administering the candidate (control group), measuring desmosterol levels, amyloid beta levels and gelsolin levels in blood of one or a plurality of individuals of the other group after the candidate is administered (candidate-administered group), and comparing the levels of those groups. In this instance, the candidate drug efficacy can be evaluated based on an indicator of being potential for the candidate to be effective in treating Alzheimer's disease or mild cognitive impairment when the desmosterol level in blood of the candidate-administered group is higher than the level of the control group, Aβx-42 or Aβx-42/Aβx-40 in blood of the candidate-administered group is higher than that of the control group, and the gelsolin level in blood of the candidate-administered group is higher than the level of the control group.

The method for aiding diagnosis of Alzheimer's disease or mild cognitive impairment of the present invention provides an indicator for diagnosis by measuring a desmosterol level, an amyloid beta level and a gelsolin level in a blood sample of a subject which is suspected to have Alzheimer's disease or mild cognitive impairment and comparing reference values therewith. More specifically, the method of the present invention provides an indicator for potentially having Alzheimer's disease or mild cognitive impairment when the desmosterol level in blood of the subject is lower than a reference value, Aβx-42 or Aβx-42/Aβx-40 in blood of the subject is lower than a reference value, and the gelsolin level in blood of the subject is lower than a reference value. The reference value of desmosterol level in blood, the reference value of Aβx-42 or Aβx-42/Aβx-40 in blood and the reference value of gelsolin level in blood can be determined by referring to the values of a patient definitely diagnosed with Alzheimer's disease or mild cognitive impairment.

The method for diagnosing Alzheimer's disease or mild cognitive impairment of the present invention makes identification by measuring desmosterol in blood, an amyloid beta level and a gelsolin level in blood of a subject which is suspected to have Alzheimer's disease or mild cognitive impairment and comparing reference values therewith. More specifically, when the desmosterol level in blood of the subject is lower than a reference value, Aβx-42 or Aβx-42/Aβx-40 in blood of the subject is lower than a reference value, and the gelsolin level in blood of the subject is lower than a reference value, the subject is identified as having Alzheimer's disease or mild cognitive impairment. The reference value of desmosterol level in blood, the reference value of Aβx-42 or Aβx-42/Aβx-40 in blood and the reverence value of gelsolin level in blood are as described above.

The method for selecting a patient which is likely to benefit from the therapeutic effect of a candidate for a therapeutic agent to treat Alzheimer's disease or mild cognitive impairment of the present invention makes identification by measuring desmosterol in blood, an amyloid beta level and a gelsolin level in blood of a subject which is diagnosed with Alzheimer's disease or mild cognitive impairment and comparing reference values therewith. More specifically, the selection can be made based on an indicator of a patient to be administered with the candidate for a therapeutic agent to treat Alzheimer's disease or mild cognitive impairment when the desmosterol level in blood of the subject is lower than a reference value, Aβx-42 or Aβx-42/Aβx-40 in blood of the subject is lower than a reference value, and the gelsolin level in blood of the subject is lower than a reference value. The reference value of desmosterol level in blood, the reference value of Aβx-42 or Aβx-42/Aβx-40 in blood and the reverence value of gelsolin level in blood are as described above.

The method for predicting the therapeutic effect of a candidate for a therapeutic agent to treat Alzheimer's disease or mild cognitive impairment of the present invention makes identification by measuring desmosterol, an amyloid beta level and a gelsolin level in blood of a subject which is diagnosed with Alzheimer's disease or mild cognitive impairment and comparing reference values therewith. More specifically, the prediction can be made based on an indicator of being potential for the candidate to be effective in treating Alzheimer's disease or mild cognitive impairment when the desmosterol level in blood of the subject is lower than a reference value, Aβx-42 or Aβx-42/Aβx-40 in blood of the subject is lower than a reference value, and the gelsolin level in blood of the subject is lower than a reference value. The reference value of desmosterol level in blood, the reference value of Aβx-42 or Aβx-42/Aβx-40 in blood and the reverence value of gelsolin level in blood are as described above.

The candidate for a therapeutic agent to treat Alzheimer's disease or mild cognitive impairment of the present invention is not particularly limited, and is preferably as described above.

The method, which uses a desmosterol level and a gelsolin level in blood as the biomarkers, is described.

The method for evaluating an effect of a candidate for a therapeutic agent to treat Alzheimer's disease or mild cognitive impairment of the present invention targets a non-human animal or a human. Specifics are as described above.

The effect of a candidate can be evaluated when a desmosterol level and a gelsolin level in blood of a non-human animal or a human of the same individual are measured before and after the candidate is administered and the levels are compared.

The method for measuring a desmosterol level and a gelsolin level in blood is as described above.

The candidate drug efficacy can be evaluated based on an indicator of being potential for the candidate to be effective in treating Alzheimer's disease or mild cognitive impairment when the desmosterol level in blood after the candidate is administered is higher than the desmosterol level in blood before the candidate is administered, and the gelsolin level in blood after the candidate is administered is higher than the gelsolin level in blood before the candidate is administered.

Also, using non-human animals of different individuals, the effect of a candidate can be evaluated by measuring desmosterol levels and gelsolin levels in blood of one or a plurality of individuals in one group without administering the candidate (control group), measuring desmosterol levels and gelsolin levels in blood of one or a plurality of individuals of the other group after the candidate is administered (candidate-administered group), and comparing the levels of those groups. In this instance, the candidate drug efficacy can be evaluated based on an indicator of being potential for the candidate to be effective in treating Alzheimer's disease or mild cognitive impairment when the desmosterol level in blood of the candidate-administered group is higher than the level of the control group, and the gelsolin level in blood of the candidate-administered group is higher than the level of the control group.

The method for aiding diagnosis of Alzheimer's disease or mild cognitive impairment of the present invention provides an indicator for diagnosis by measuring a desmosterol level and a gelsolin level in a blood sample of a subject which is suspected to have Alzheimer's disease or mild cognitive impairment and comparing reference values therewith. More specifically, the method of the present invention provides an indicator for potentially having Alzheimer's disease or mild cognitive impairment when the desmosterol level in blood of the subject is lower than a reference value, and the gelsolin level in blood of the subject is lower than a reference value. The reference value of desmosterol level in blood and the reference value of gelsolin level in blood can be determined by referring to the values of a patient definitely diagnosed with Alzheimer's disease or mild cognitive impairment.

The method for diagnosing Alzheimer's disease or mild cognitive impairment of the present invention makes identification by measuring a desmosterol level in blood and a gelsolin level in blood of a subject which is suspected to have Alzheimer's disease or mild cognitive impairment and comparing reference values therewith. More specifically, when the desmosterol level in blood of the subject is lower than a reference value, and the gelsolin level in blood of the subject is lower than a reference value, the subject is identified as having Alzheimer's disease or mild cognitive impairment. The reference value of desmosterol level in blood and the reference value of gelsolin level in blood are as described above.

The method for selecting a patient which is likely to benefit from the therapeutic effect of a candidate for a therapeutic agent to treat Alzheimer's disease or mild cognitive impairment of the present invention makes identification by measuring a desmosterol level in blood and a gelsolin level in blood of a subject which is diagnosed with Alzheimer's disease or mild cognitive impairment and comparing reference values therewith. More specifically, the selection can be made based on an indicator of a patient to be administered with the candidate for a therapeutic agent to treat Alzheimer's disease or mild cognitive impairment when the desmosterol level in blood of the subject is lower than a reference value, and the gelsolin level in blood of the subject is lower than a reference value. The reference value of desmosterol level in blood and the reference value of gelsolin level in blood are as described above.

The method for predicting the therapeutic effect of a candidate for a therapeutic agent to treat Alzheimer's disease or mild cognitive impairment of the present invention makes identification by measuring a desmosterol level and a gelsolin level in blood of a subject which is diagnosed with Alzheimer's disease and comparing reference values therewith. More specifically, the prediction can be made based on an indicator of being potential for the candidate to be effective in treating Alzheimer's disease or mild cognitive impairment when the desmosterol level in blood of the subject is lower than a reference value, and the gelsolin level in blood of the subject is lower than a reference value. The reference value of desmosterol level in blood and the reference value of gelsolin level in blood are as described above.

The candidate for a therapeutic agent to treat Alzheimer's disease or mild cognitive impairment of the present invention is not particularly limited, and preferably as described above.

EXAMPLES

Example 1

Measurement of Desmosterol Levels in Blood of Healthy Elderly People and Patients with Alzheimer's Disease Sample Plasma of healthy elderly people (10 cases) and patients with Alzheimer's disease (10 cases) were used as samples.

Measurement of Desmosterol

To 25 μl of plasma were added as the internal standards 100 μL of 500 ng/ml of desmosterol-d6 (purchased from Avanti Polar Lipids, Inc.) and 100 μL of 200 μg/ml of cholesterol-d7 (purchased from KANTO CHEMICAL CO., INC.), and 100 μL, of a 50% potassium hydroxide aqueous solution was further added thereto, and the incubation was carried out at 70° C. for 60 minutes. Subsequently, 2 mL of hexane and 0.5 mL of phosphate buffered saline (pH 6.8) were added thereto, stirred and centrifuged, and the hexane layer was collected. The extraction operation was repeated twice. After combining the hexane layers obtained, the solvent was dried by evaporation using a nitrogen gas. The pellet was dissolved in ethanol and the solution was subjected to liquid chromatography/atmospheric pressure chemical ionization mass spectrometry (LC/APCI-MS).

The apparatus for LC/APCI-MS used was an LC-20AD system (manufactured by Shimadzu Corporation) equipped with an autosampler SIL-20AC, a column oven CTO-20AC and a quadrupole mass spectrometer LCMS-2010EV. The column temperature was set at 50° C., using YMC-Pack Pro C18 RS column (purchased from YMC Co., Ltd.) having an internal diameter of 4.6 mm and a length of 250 mm as a column. The mobile phase used was a mixed solvent of water and methanol (flow rate 1 ml/min.). More specifically, solution A (water:methanol=50:50) and solution B (methanol) were used, with B being 85% during 0 to 45 minutes, 100% during 45 to 55 minutes, and 85% during 55 to 70 minutes.

The MS analysis was carried out in Selective Ion Monitoring (SIM) mode, using, as the monitoring ions, m/z 369.3, 376.3, 367.3 and 373.3 (corresponding to cholesterol, cholesterol-d7, desmosterol and desmosterol-d6, respectively). The concentration of each sample was calculated based on the calibration curve of the subject to be measured.

The results are shown in the following Tables 1 and 2. The desmosterol levels in plasma of the patients with Alzheimer's disease were found to have been lower than the level of healthy elderly people.

TABLE 1

| Healthy elderly people | | |
| --- | --- | --- |
| Sex | Age | Desmosterol (ng/mL) |
| F | 63 | 931 |
| M | 72 | 865 |
| F | 66 | 880 |
| M | 68 | 886 |
| M | 71 | 854 |
| F | 60 | 1261 |
| M | 61 | 500 |
| M | 69 | 795 |
| F | 74 | 621 |
| F | 71 | 889 |
| Average | 67.5 | 848 |

TABLE 2

| Patients with Alzheimer's disease | | |
| --- | --- | --- |
| Sex | Age | Desmosterol (ng/mL) |
| M | 80 | 367 |
| M | 70 | 519 |
| M | 77 | 367 |
| M | 84 | 590 |
| F | 86 | 284 |
| F | 70 | 337 |
| F | 75 | 427 |
| F | 71 | 692 |
| M | 74 | 322 |

TABLE 2-continued

| Patients with Alzheimer's disease | | |
|---|---|---|
| Sex | Age | Desmosterol (ng/mL) |
| F | 90 | 433 |
| Average | 77.7 | 434 |

Example 2

Measurement of Desmosterol Levels and Amyloid Beta Levels in Blood of Healthy Elderly People and Patients with Alzheimer's Disease Sample
Plasma of healthy elderly people (10 cases) and patients with Alzheimer's disease (10 cases) were used as samples.
Measurement of Desmosterol
The measurement was carried out by the same method as in Example 1.
Measurement of Aβx-40 and Aβx-42
The concentrations of Aβx-40 and Aβx-42 in blood were measured using a WAKO Aβx-40 ELISA kit (Wako Pure Chemical Industries, Ltd.) and a WAKO Aβx-42 High sensitivity ELISA kit (Wako Pure Chemical Industries, Ltd.) in accordance with the manuals of the kits.
The results are shown in the following Tables 3 and 4.

TABLE 3

| Healthy elderly people | | | | | |
|---|---|---|---|---|---|
| Sex | Age | Desmosterol (ng/mL) | x-40 (pM) | x-42 (pM) | x-42/x-40 |
| F | 63 | 931 | 88 | 6.7 | 0.076 |
| M | 72 | 865 | 77 | 7.7 | 0.101 |
| F | 66 | 880 | 61 | 7.3 | 0.120 |
| M | 68 | 886 | 92 | 8.9 | 0.096 |
| M | 71 | 854 | 98 | 8.8 | 0.090 |
| F | 60 | 1261 | 67 | 7.2 | 0.107 |
| M | 61 | 500 | 94 | 8.5 | 0.091 |
| M | 69 | 795 | 61 | 5.9 | 0.097 |
| F | 74 | 621 | 64 | 5.5 | 0.086 |
| F | 71 | 889 | 53 | 5.1 | 0.097 |
| Average | 67.5 | 848 | 75.5 | 7.2 | 0.096 |

TABLE 4

| Patients with Alzheimer's disease | | | | | |
|---|---|---|---|---|---|
| Sex | Age | Desmosterol (ng/mL) | x-40 (pM) | x-42 (pM) | x-42/x-40 |
| M | 80 | 367 | 96 | 8.7 | 0.090 |
| M | 70 | 519 | 99 | 7.7 | 0.078 |
| M | 77 | 367 | 88 | 5.3 | 0.060 |
| M | 84 | 590 | 88 | 5.3 | 0.060 |
| F | 86 | 284 | 99 | 8.2 | 0.083 |
| F | 70 | 337 | 55 | 4.3 | 0.078 |
| F | 75 | 427 | 78 | 6.0 | 0.076 |
| F | 71 | 692 | 34 | 1.7 | 0.049 |
| M | 74 | 322 | 87 | 7.6 | 0.088 |
| F | 90 | 433 | 84 | 7.2 | 0.085 |
| Average | 77.7 | 434 | 80.9 | 6.2 | 0.075 |

Statistical Analysis
Using the above data, the Receiver Operating Characteristic Curve was used to evaluate the diagnosis accuracy of each measured value and the combinations thereof. The Receiver Operating Characteristic Curve of each of desmosterol and Aβx-42/Aβx-40 was drawn using ROC, a basic package for R. For the combination of desmosterol and Aβx-42/Aβx-40, a machine learning model called SVM (Support Vector Machine), (R package e1071) was used The evaluation was carried out by random sampling of 10 samples, as a set of training examples, from the total of 20 samples consisting of 10 samples of the healthy elderly people group and 10 samples of the group of patients with Alzheimer's disease, with the remaining 10 samples being a set of test examples. Also, the Receiver Operating Characteristic Curves of the prediction results of the test data were drawn using the ROCR package (FIG. 1). Desmosterol alone had AUC of 0.96, Aβx-42/Aβx-40 had AUC of 0.91, and the combination of desmosterol and Aβx-42/Aβx-40 had AUC of 1.

Example 3

Figure 2:
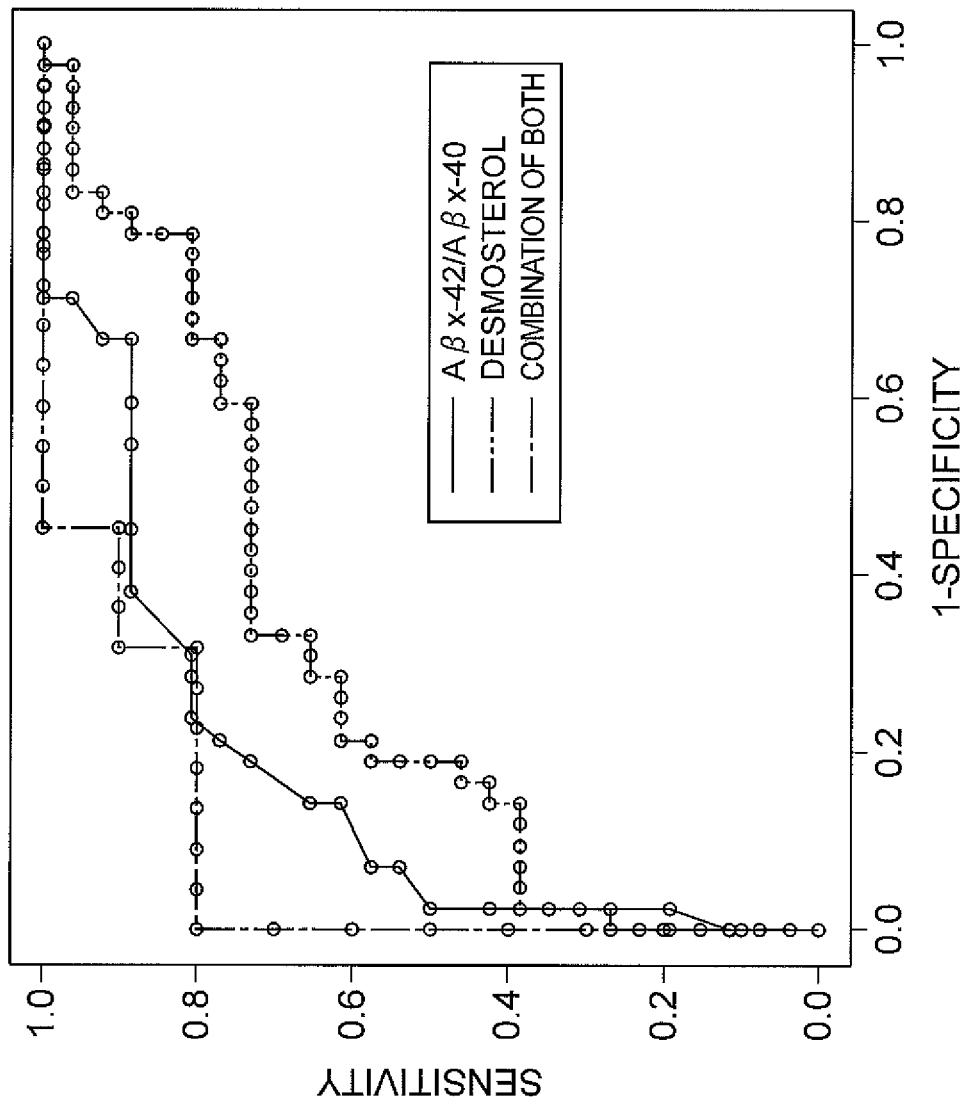
FIG. 2 is a chart showing the Receiver Operating Characteristic Curves of desmosterol, Aβx-42/Aβx-40 and the combination thereof in healthy elderly people and patients with mild cognitive impairment.

Measurement of Desmosterol Levels and Amyloid Beta Levels in Blood of Healthy Elderly People and Patients with Mild Cognitive Impairment Sample
Plasma of healthy elderly people (42 cases) and patients with mild cognitive impairment (26 cases) were used as samples.
Measurement of Desmosterol
The measurement was carried out by the same method as in Example 1.
Measurement of Aβx-40 and Aβx-42
The measurement was carried out by the same method as in Example 2.
Statistical Analysis
Using the above data, the Receiver Operating Characteristic Curve was used as in Example 2 to evaluate the diagnosis accuracy of each measured value and the combinations thereof. The evaluation was carried out by random sampling of 34 samples, as a set of training examples, from the total of 68 samples consisting of 42 samples of the healthy elderly people group and 26 samples of the group of patients with mild cognitive impairment, with the remaining 34 samples being a set of test examples. Also, the Receiver Operating Characteristic Curves of the prediction results of the test data were drawn using the ROCR package (FIG. 2). Desmosterol alone had AUC of 0.71, Aβx-42/Aβx-40 had AUC of 0.84, and the combination of desmosterol and Aβx-42/Aβx-40 had AUC of 0.92.

Example 4

Measurement of Desmosterol Levels, Amyloid Beta Levels and Gelsolin Levels in Blood of Healthy Elderly People, Patients with Alzheimer's Disease and Patients with Mild Cognitive Impairment Sample
Plasma of healthy elderly people (37 cases), patients with Alzheimer's disease (39 cases) and patients with mild cognitive impairment (26 cases) were used as samples.
Measurement of Desmosterol
The measurement was carried out by the same method as in Example 1.
Measurement of Aβx-40 and Aβx-42
The measurement was carried out by the same method as in Example 2.

Measurement of Gelsolin

Figure 3:
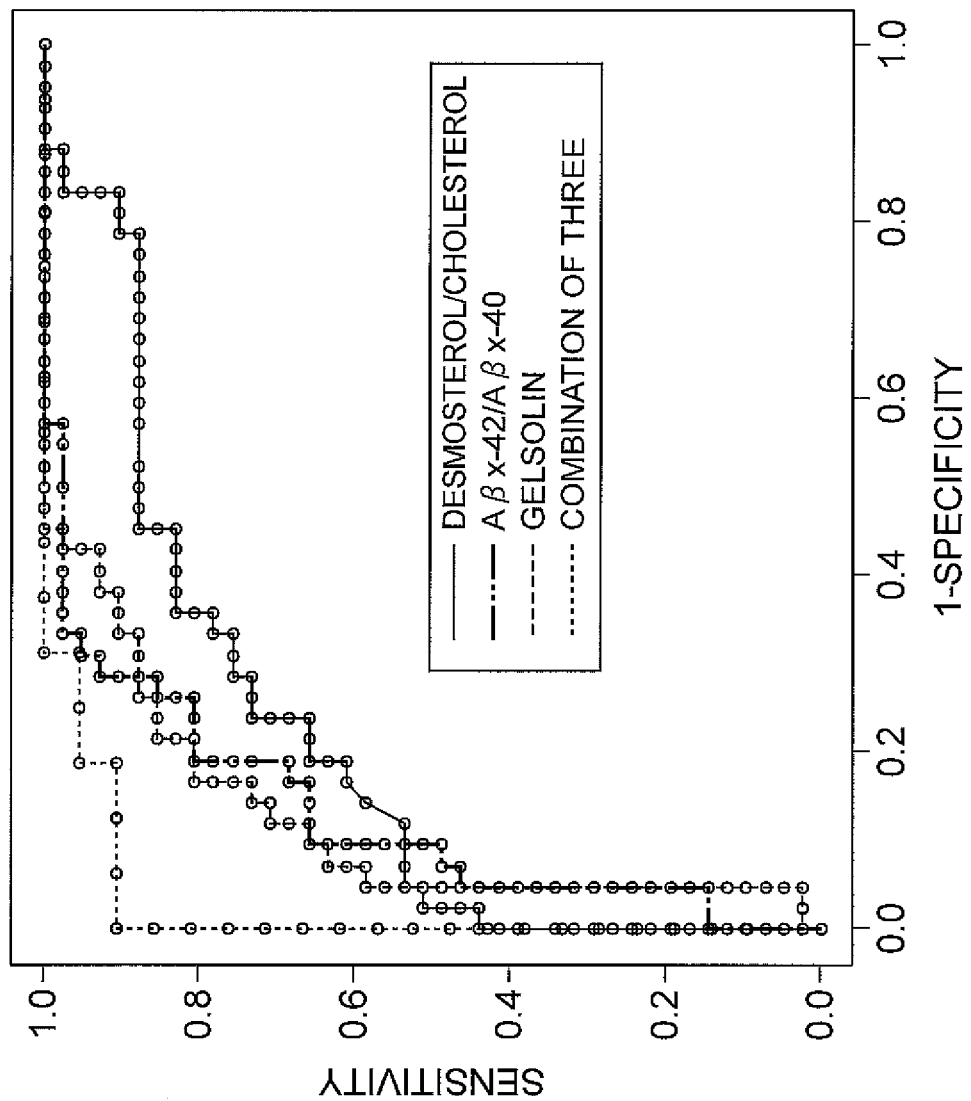
FIG. 3 is a chart showing the Receiver Operating Characteristic Curves of desmosterol/cholesterol, Aβx-42/Aβx-40, gelsolin and the combination thereof in healthy elderly people and patients with Alzheimer's disease.

The concentration of gelsolin in blood was measured using a gelsolin ELISA kit for human (USCN Life Science Inc.) in accordance with the manual of the kit Statistical Analysis Using the above data, the Receiver Operating Characteristic Curve was used as in Example 2 to evaluate the diagnosis accuracy of each measured value and the combinations thereof. The evaluation was carried out by random sampling of 38 samples, as a set of training examples, from the total of 76 samples consisting of 37 samples of the healthy elderly people group and 39 samples of the patients with Alzheimer's disease group, with the remaining 38 samples being a set of test examples. The Receiver Operating Characteristic Curves of the prediction results of the test data were drawn using the ROCR package (FIG. 3). Desmosterollcholesterol had AUC of 0.80, Aβx-42/Aβx-40 had AUC of 0.88, gelsolin had AUC of 0.88, and the combination of three had AUC of 0.98. The combination of three had a sensitivity of 90% when the specificity is 100%.

Figure 4:
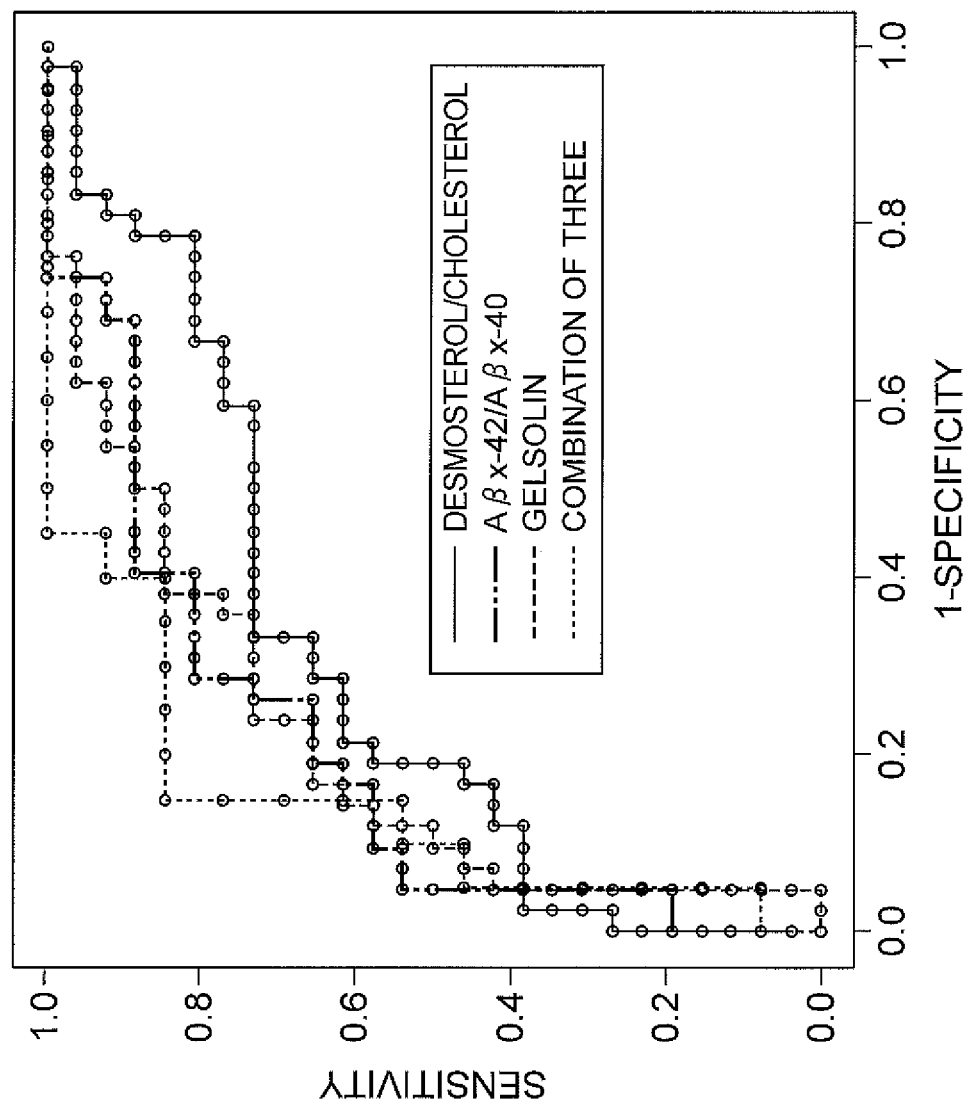
FIG. 4 is a chart showing the Receiver Operating Characteristic Curves of desmosterol/cholesterol, Aβx-42/Aβx-40, gelsolin and the combination thereof in healthy elderly people and patients with mild cognitive impairment

Also, the evaluation was carried out by random sampling of 32 samples, as a set of training examples, from the total of 63 samples consisting of 37 samples of the healthy elderly people group and 26 samples of the patients with mild cognitive impairment group, with the remaining 31 samples being a set of test examples. The Receiver Operating Characteristic Curves of the prediction results of the test data were drawn using the ROCR package (FIG. 4). Desmosterol/cholesterol had AUC of 0.71, Aβx-42/Aβx-40 had AUC of 0.81, gelsolin had AUC of 0.80, and the combination of three had AUC of 0.86. The combination of three had a sensitivity of 85% when the specificity is 85%.

Example 5

Measurement of Desmosterol Levels and Gelsolin Levels in Blood of Healthy Elderly People, Patients with Alzheimer's Disease and Patients with Mild Cognitive Impairment Sample Plasma of healthy elderly people (42 cases), patients with Alzheimer's disease (41 cases) and patients with mild cognitive impairment (26 cases) were used as samples.

Measurement of Desmosterol

The measurement was carried out by the same method as in Example 1.

Measurement of Gelsolin

The measurement was carried out by the same method as in Example 4.

Statistical Analysis

Figure 5:
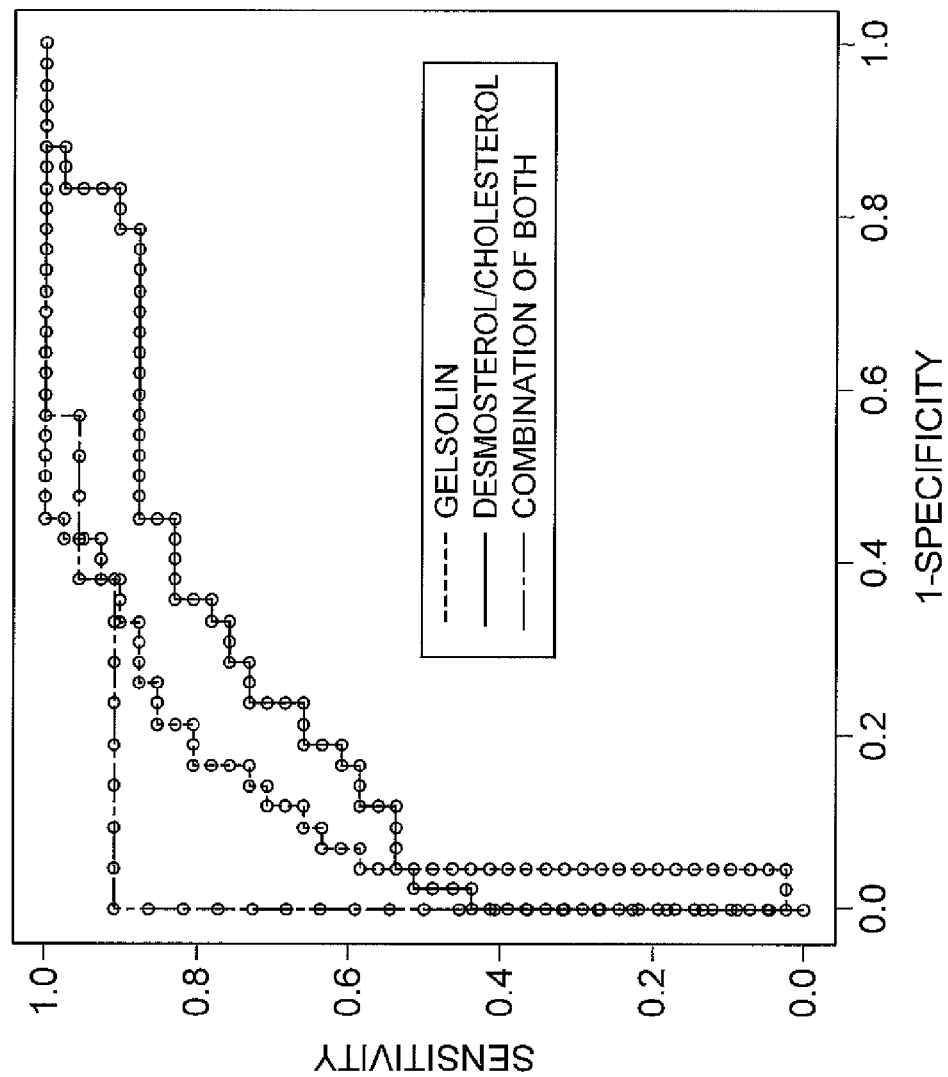
FIG. 5 is a chart showing the Receiver Operating Characteristic Curves of desmosterol/cholesterol, gelsolin and the combination thereof in healthy elderly people and patients with Alzheimer's disease.

Using the above data, the Receiver Operating Characteristic Curve was used as in Example 2 to evaluate the diagnosis accuracy of each measured value and the combinations thereof. The evaluation was carried out by random sampling of 42 samples, as a set of training examples, from the total of 83 samples consisting of 42 samples of the healthy elderly people group and 41 samples of the patients with Alzheimer's disease group, with the remaining 41 samples being a set of test examples. The Receiver Operating Characteristic Curves of the prediction results of the test data were drawn using the ROCR package (FIG. 5). Desmosterol/cholesterol had AUC of 0.80, gelsolin had AUC of 0.88, and the combination of both had AUC of 0.96.

Figure 6:
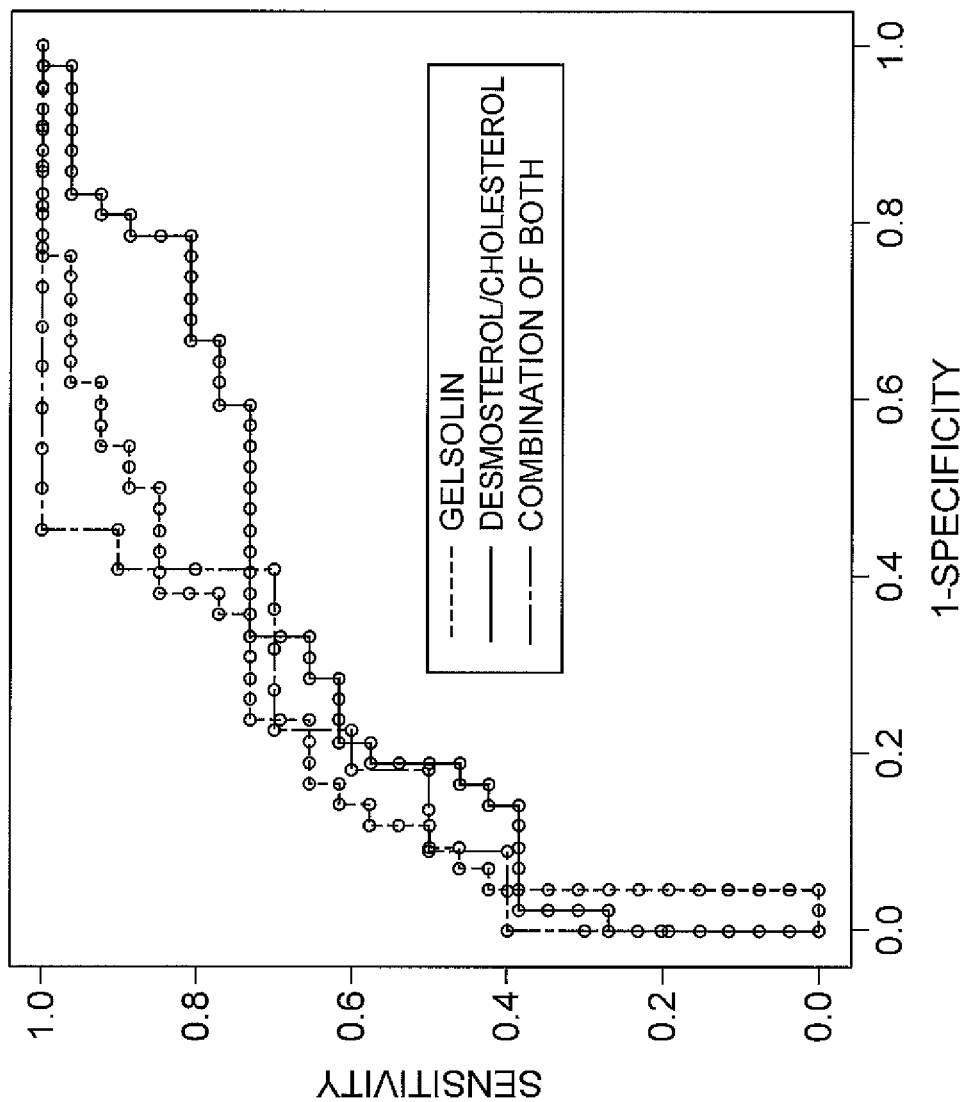
FIG. 6 is a chart showing the Receiver Operating Characteristic Curves of desmosterol/cholesterol, gelsolin and the combination thereof in healthy elderly people and patients with mild cognitive impairment.

Also, the evaluation was carried out by random sampling of 34 samples, as a set of training examples, from the total of 68 samples consisting of 42 samples of the healthy elderly people group and 26 samples of the patients with mild cognitive impairment group, with the remaining 34 samples being a set of test examples. The Receiver Operating Characteristic Curves of the prediction results of the test data were drawn using the ROCR package (FIG. 6). Desmosterol/cholesterol had AUC of 0.71, gelsolin had AUC of 0.80 and the combination of both had AUC of 0.82.

Example 6

Measurement of Desmosterol Levels in Blood of Healthy Elderly People and Patients with Mild Cognitive Impairment Sample Plasma of healthy elderly people (42 cases) and patients with mild cognitive impairment (26 cases) were used as samples.

Measurement of Desmosterol

Figure 7:
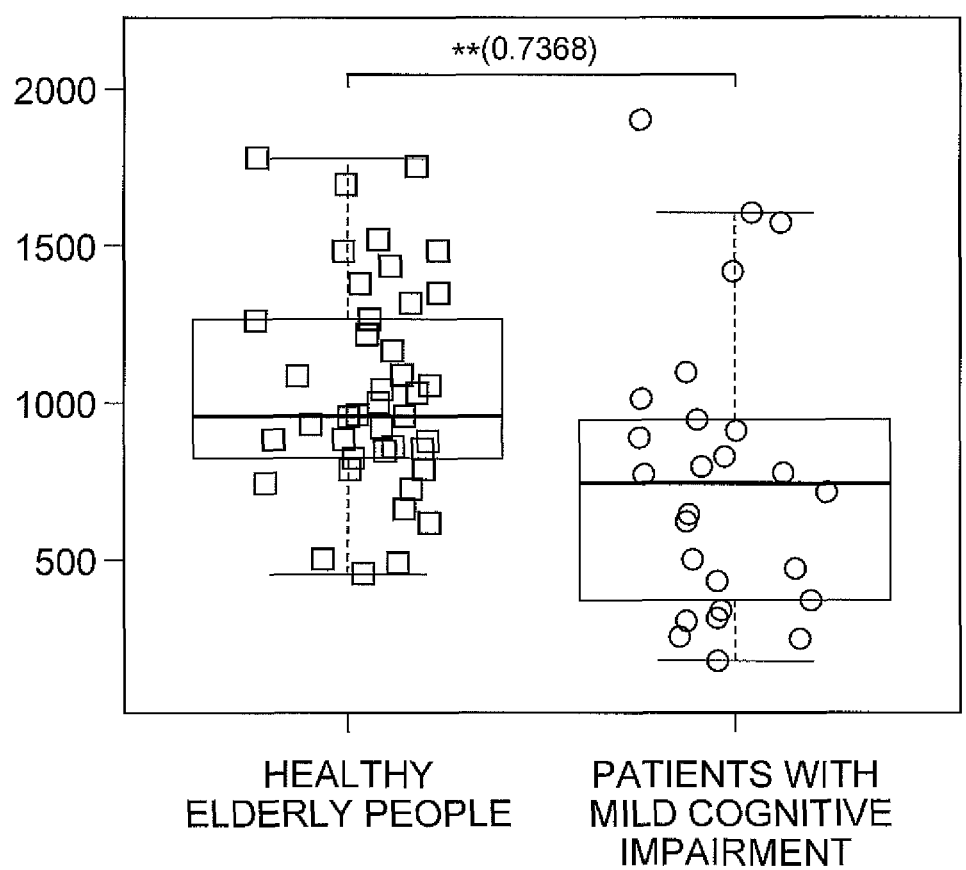
FIG. 7 is a chart showing desmosterol levels in healthy elderly people and patients with mild cognitive impairment In the chart, the thick bar represents the median value. The fold of change in patients with mild cognitive impairment against healthy elderly people is 0.7368.

The measurement was carried out by the same method as in Example 1. The desmosterol levels in blood of healthy elderly people and patients with mild cognitive impairment were shown in FIG. 7. The average plasma desmosterol level of healthy elderly people was 1046 ng/ml and the average plasma desmosterol level of patients with mild cognitive impairment was 770 ng/ml. Significant difference was found between both groups (p<0.01; t-test).

Statistical Analysis

Figure 8:
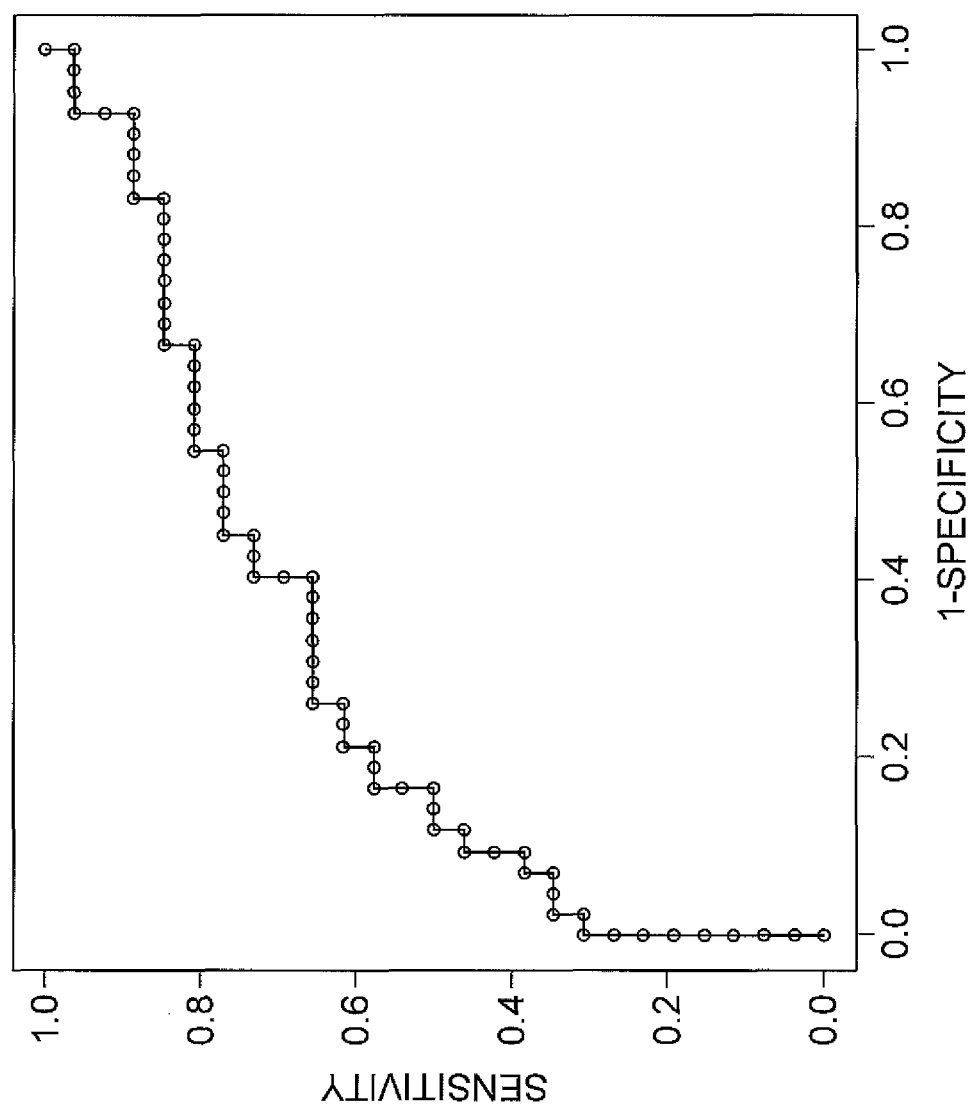
FIG. 8 is a chart showing the Receiver Operating Characteristic Curves of desmosterol in healthy elderly people and patients with mild cognitive impairment.

Using the above data, the Receiver Operating Characteristic Curve was used as hi Example 2 to evaluate the diagnosis accuracy. The evaluation was carried out by random sampling of 34 samples, as a set of training examples, from the total of 68 samples consisting of 42 samples of the healthy elderly people group and 26 samples of the patients with mild cognitive impairment group, with the remaining 34 samples being a set of test examples. The Receiver Operating Characteristic Curves of the prediction results of the test data were drawn using the ROCR package (FIG. 8). AUC was 0.72.

The invention claimed is:

1. A method for evaluating an effect of a candidate on a desmosterol level and an amyloid beta level in blood, the method comprising:
   measuring a desmosterol level and an amyloid beta level in blood of a human or nonhuman animal;
   administering a candidate to the human or non-human animal;
   measuring a desmosterol level and an amyloid beta level in blood of the human or nonhuman animal after the candidate is administered; and
   determining whether the desmosterol level in blood of the human or non-human animal after the candidate is administered is higher than the level before the candidate is administered, and the Aβx-42 or Aβx-42/Aβx-40 level in blood of the human or non-human animal after the candidate is administered is higher than that before the candidate is administered.

2. The method of claim 1, wherein the method comprises:
   measuring a desmosterol level, an amyloid beta level and a gelsolin level in blood of a human or non-human animal;
   administering a candidate to the human or non-human animal;
   measuring a desmosterol level, an amyloid beta level and a gelsolin level in blood of the human or non-human animal after the candidate is administered; and determining whether the desmosterol level in blood of the human or non-human animal after the candidate is administered is higher than the desmosterol level in blood before the candidate is administered, the Aβx-42 or Aβx-42/Aβx-40 level in blood of the human or non-human animal after the candidate is administered is higher than that before the candidate is administered, and the gelsolin level in blood of the human or non-human animal after the candidate is administered is higher than the gelsolin level in blood before the candidate is administered.

3. A method for evaluating an effect of a candidate on desmosterol level and an amyloid beta level in blood, the method comprising:
measuring a desmosterol level and an amyloid beta level in blood of a first human or nonhuman animal;
administering a candidate to a second human or non-human animal;
measuring a desmosterol level and an amyloid beta level in blood of the second human or non-human animal after the candidate is administered; and
determining whether the desmosterol level in blood of the second human or non-human animal after the candidate is administered is higher than the desmosterol level in blood of the first human or non-human animal to which the candidate is not administered, and the Aβx-42 or Aβx-42/Aβx-40 level in blood of the second human or non-human animal after the candidate is administered is higher than the Aβx-42 or Aβx-42/Aβx-40 level in blood of the first human or non-human animal to which the candidate is not administered.

4. The method of claim 3, wherein the method comprises:
measuring a desmosterol level, an amyloid beta level and a gelsolin level in blood of a first human or non-human animal;
administering a candidate to a second human or non-human animal;
measuring a desmosterol level, an amyloid beta level and a gelsolin level in blood of the second human or non-human animal after the candidate is administered; and
determining whether the desmosterol level in blood of the second human or non-human animal after the candidate is administered is higher than the desmosterol level in blood of the first human or non-human animal to which the candidate is not administered, the Aβx-42 or Aβx-42/Aβx-40 level in blood of the second human or non-human animal after the candidate is administered is higher than the Aβx-42 or Aβx-42/Aβx-40 level in blood of the first human or non-human animal to which the candidate is not administered, and the gelsolin level in blood of the second human or non-human animal after the candidate is administered is higher than the gelsolin level in blood of the first human or non-human animal to which the candidate is not administered.

5. A method for administering a candidate therapeutic agent to treat Alzheimer's disease or mild cognitive impairment to a patient in need thereof, the method comprising:
measuring in a blood sample of a patient a desmosterol level that is lower than a reference value; and
administering to the patient a candidate therapeutic agent to treat Alzheimer's disease or mild cognitive impairment.

6. The method of claim 5, wherein the method comprises:
measuring in a blood sample of a patient a desmosterol level that is lower than a reference value and an Aβx-42 or Aβx-42/Aβx-40 level that is lower than a reference value; and
administering to the patient a candidate for a therapeutic agent to treat Alzheimer's disease or mild cognitive impairment.

7. The method of claim 5, wherein the method comprises:
measuring in a blood sample of a patient a desmosterol level that is lower than a reference value, an Aβx-42 or Aβx-42/Aβx-40 level that is lower than a reference value, and a gelsolin level that is lower than a reference value; and
administering to the patient a candidate for a therapeutic agent to treat Alzheimer's disease or mild cognitive impairment.

8. The method of claim 5, wherein the method comprises:
measuring in a blood sample of a patient a desmosterol level that is lower than a reference value and a gelsolin level that is lower than a reference value; and
administering to the patient a candidate for a therapeutic agent to treat Alzheimer's disease or mild cognitive impairment.

* * * * *